United States Patent [19]

Gernon

[11] Patent Number: 5,491,247

[45] Date of Patent: Feb. 13, 1996

[54] PREPARATION OF A PRECIOUS METAL SALT OF A NONOXIDIZING ACID BY DIRECT REACTION

[75] Inventor: Michael D. Gernon, Upper Providence, Pa.

[73] Assignee: Elf Atochem North America, Inc., Philadelphia, Pa.

[21] Appl. No.: 338,069

[22] Filed: Nov. 14, 1994

[51] Int. Cl.$^6$ .............................. C07F 1/08; C07F 15/00
[52] U.S. Cl. .............................. 556/113; 556/7; 556/114; 556/116; 556/136
[58] Field of Search ...................... 556/136, 113, 556/114, 116, 7

[56] References Cited

U.S. PATENT DOCUMENTS

| | | | |
|---|---|---|---|
| 2,433,395 | 12/1947 | Proell et al. | 260/513 |
| 2,433,396 | 12/1947 | Proell et al. | 260/513 |
| 2,525,942 | 10/1950 | Proell et al. | 204/45 |
| 4,465,635 | 8/1984 | Chang et al. | 260/414 |
| 4,673,472 | 6/1987 | Morrissey et al. | 204/44.6 |
| 5,160,600 | 11/1992 | Patel et al. | 205/169 |
| 5,162,555 | 1/1992 | Remmers | 556/85 |

*Primary Examiner*—Porfirio Nazario-Gonzales

[57] ABSTRACT

A process is disclosed for the manufacture of precious metal salts by the direct reaction of a precious metal and an oxidizing agent in the presence of a nonoxidizing acid.

23 Claims, No Drawings

PREPARATION OF A PRECIOUS METAL SALT OF A NONOXIDIZING ACID BY DIRECT REACTION

BACKGROUND OF THE INVENTION

This invention concerns the preparation of a precious metal salt by the direct oxidation of such metal in a nonoxidizing acid. More particularly, it concerns the one-step synthesis of a precious metal salt via the direct reaction of such metal with an oxidizing agent in the presence of a nonoxidizing acid.

THE PRIOR ART

The synthesis of precious metal salts (particularly silver salts) of nonoxidizing acids is generally carried out using a series of steps.

For example, the preparation of silver salts of nonoxidizing acids has been accomplished by the steps of:

1) formation of silver nitrate by treatment of silver metal (Ag) with nitric acid;
2) formation of silver oxide (or silver carbonate) by the addition of caustic (or sodium carbonate) to silver nitrate; and
3) acidification of silver oxide (or silver carbonate) with the nonoxidizing acid of interest.

Silver metal can be oxidatively dissolved at a reasonable rate by a number of oxidizing acids, (e.g., nitric acid), but the oxidation of silver metal by pure nonoxidizing acids, (e.g., methanesulfonic acid) is impractically slow.

It is possible to prepare the silver salts of certain nonoxidizing acids (e.g., HCN) by treatment of silver metal with an oxidant in an alkaline solution containing dissolved alkaline salts of the said nonoxidizing acid, but such procedures require that the conjugate base (anion) of the acid be strongly complexing. A strongly complexing anion can be defined as one which is capable of forming a readily isolable silver double salt (e.g., $KAgCN_2$), and the conjugate acids of such anions normally have aqueous $pK_a$ values of 9.0 or greater. Strongly complexing anions as used in aqueous alkaline oxidation media are well known in the art of making precious metal salts, and such systems are readily distinguishable from systems which, like the invention disclosed herein, employ strongly acidic reaction conditions. To date, an economical, one-step oxidation method (employing an acidic reaction medium) has not been found practical for the preparation of precious metal salts of nonoxidizing acids, and expensive multistep procedures, such as outlined above, are generally necessary for the preparation of these compounds.

A great deal of previous work has dealt with the preparation of aqueous solutions of base metal methanesulfonates. Aqueous solutions of stannous and lead methanesulfonates are particularly significant in that such solutions are used to prepare industrially important Sn/Pb electroplating baths. Indeed, Remmers et al. (U.S. Pat. No. 5,162,555) claim a process wherein aqueous solutions of non-ferrous methanesulfonates, particularly $Sn(OMs)_2$, can be prepared by reacting a mixture of a non-ferrous metal and methanesulfonic acid with molecular oxygen or gases which contain molecular oxygen. Remmer et al. (U.S. Pat. No. 5,162,555) do not discuss the preparation of an aqueous solution of a precious metal (Pt, Pd, Ag, Au, Ir, Rh, Os, Ru) methanesulfonate by the reaction of a mixture of a precious metal and methanesulfonic acid with oxygen or air, and, indeed, we have found that such procedures are completely impractical. Clearly, Remmers et al. did not anticipate nor were they concerned with the unique problems associated with the oxidation of precious metals.

STATEMENT OF THE INVENTION

This invention is a process for the direct synthesis of a precious metal salt of a nonoxidizing acid comprising reacting together a precious metal and an oxidizing agent in the presence of a nonoxidizing acid of interest.

DETAILED DESCRIPTION OF THE INVENTION

This invention relates to the preparation of a precious metal salt of a nonoxidizing acid preferably via the addition of an oxidizing agent(s) to a heterogeneous mixture of such metal and a desired nonoxidizing acid (aqueous or anhydrous). For reactions of practical importance, this invention pertains principally to reaction media wherein an anhydrous or aqueous solution of the nonoxidizing acid employed is neutralized to an extent of less than 99% and, more preferably, neutralized less than 10% to 0%. To further define a nonoxidizing acid, it may be distinguished from an oxidizing acid which can be defined as an acid which promotes oxidation to an extent greater than that which is due solely to the protonic strength of the acid. Nitric acid ($HNO_3$), perchloric acid ($HClO_4$), and fuming sulfuric acid ($H_2SO_4/SO_3$) are commonly used oxidizing acids, and, for the purposes of this invention, the halogen acids (HF, HCl, HBr, HI) are also considered oxidizing.

Hereinafter, the details of the invention will be described using silver metal to represent the preferred precious metal of this invention. The silver salt is initially obtained in solution with some amount of excess acid. This solution can be used as is, or a pure silver salt can be obtained by traditional purification methods. Of the purification methods available, solution concentration followed by solvent washing of the partially precipitated salt is particularly useful.

The oxidizing agents which can be used in this process include any and all chemicals or mixtures thereof with sufficient chemical potential to oxidize silver (or the precious metal of interest). Ideally, the oxidizing agents are such that as a result of the oxidation process they decompose to produce water, the nonoxidizing acid used in the process, and/or other by-products which can be easily removed from the product metal salt. An aqueous solution of hydrogen peroxide is the preferred oxidizing agent. Dialkanesulfonyl peroxides, though more difficult to obtain than hydrogen peroxide, also work well.

The precious metal employed is preferably relatively pure, as metallic impurities less noble than the metal used will be oxidized selectively. Specifically, the precious metals of this invention are silver, platinum, palladium, gold, iridium, rhodium, osmium and ruthenium. These metals can be used in any physical form, but the specific surface area (SSA) of the precious metal employed should be as high as possible. The rate of a solid-liquid heterogeneous reaction, (e.g., the one disclosed herein) is proportional to the surface area of the insoluble solid reactant, and those forms of precious metal with relatively high surface area are preferred for favoring reactions which proceed at practical rates. Generally, an SSA of 100 $cm^2$ per gram is sufficient. Silver powders (SSA=10,000 $cm^2$) work well, but the average base cost of such material is too high to allow for an economically competitive synthesis. Meshed silver needles (available directly from silver refineries, SSA= 50 to 600 cm$^2$) are ideal in that both sufficient surface area and relatively low cost are obtained. Silver needles are produced by the electrocrystallization of silver during the silver ore refining process. Silver metal of satisfactory surface area may also be prepared by electrodeposition of silver on a number of cathode materials. Other practical forms of silver for this invention include silver popcorn (i.e., molten silver which is solidified by rapid addition to a liquid cooling medium), silver shot, and mechanically chopped pieces of silver. Basically the use of any form of precious metal with a surface area which is sufficient to allow the reaction to proceed at a reasonable rate, is preferred.

If desired, the process of this invention may be combined or incorporated into a refining process for precious metal ores. For example, the refining process for silver may utilize the instant process to provide directly a silver salt of a nonoxidizing acid such as silver mesylate. Furthermore, in nature, silver occurs as a mixture of silver metal, silver chloride and/or silver sulfide. Again, the instant process may be used, in whole or in part, to process the silver metal in native silver ores.

The nonoxidizing acids which are used for the process of this invention include all those which are both stable to the oxidizing conditions of the reaction and which allow for sufficient aqueous solubility of the salt produced. The need for acid stability in the presence of the oxidizing agent(s) employed is obvious. In addition, if the reaction is to proceed at a reasonable rate, the product salt must have some solubility in the aqueous reaction medium. Low salt solubility can result in insoluble layers of salt forming on the surface of the reacting metal, and such insoluble layers will tend to retard the reaction by reducing contact between the metal and the oxidizing agent(s). The acid will have an aqueous $pK_a$ value of less than 8 (see compilations of acid dissociation constants in e.g., CRC Handbook of Chemistry and Physics), and the complexing properties of the conjugate base of the acid will generally not be important. Alkanesulfonic acids are particularly preferred in that silver alkanesulfonates are readily dissolved by aqueous solutions of the corresponding alkanesulfonic acids. Useful sulfonic acids include linear $C_1$–$C_{20}$, preferably $C_1$–$C_3$, alkanesulfonic acids, and branched chain $C_3$–$C_{40}$ alkanesulfonic acids. These acids also may have functional substituent radicals on the alkane group. The substituent radicals will include, for example, hydroxyl, keto and nitro radicals. Some specific examples, other than the most preferred methanesulfonic acid, include isethionic acid (2-hydroxyethanesulfonic acid), 2-hydroxypropanesulfonic acid, ethanesulfonic acid, propanesulfonic acid, fluoboric acid, and the like.

The temperature of the reaction is maintained at about 5° C. to about 150° C., preferably between 10° C. and 80° C. Lower temperatures can be used, but the reaction occurs more slowly and problems may result from a decreased solubility of the silver salt being prepared. Temperatures above 80° C. can also be used, but problems arising from instability of the oxidizing agent and/or the reaction medium may become significant. In particular, hydrogen peroxide is prone to spontaneous degradation to oxygen at temperatures above 80° C.

A particularly preferred embodiment of the current invention involves the addition of 30% aqueous hydrogen peroxide ($H_2O_2$) to a stirred mixture of metallic silver needles (−60 to +100 mesh, Handy & Harmon) and 70% aqueous methanesulfonic acid (MSA—1752 grade, Elf Atochem North America, Inc.) The equation for the reaction is as follows:

$$2\,Ag + 2CH_3SO_2OH + H_2O_2 \rightarrow 2\,AgO_3SCH_3 + 2H_2O$$

The peroxide addition is preferably carried out at room temperature with no external heating or cooling. The rate of the peroxide addition is controlled so that the temperature of the reaction does not rise above 40° C. The acid/silver ratio is approximately 200 ml of 70% MSA (approx. 2 mole) per 110 grams of silver metal (approx. 1 mole). A two to threefold excess of hydrogen peroxide is normally employed. Following peroxide addition, the reaction may be checked at 30 minute intervals for excess oxidant level (NaI color test). The time necessary for complete reaction of the peroxide varies depending on the surface area and exact form of the silver metal used.

Following the complete consumption of the hydrogen peroxide, the solution may be freed from excess silver and residual solids by filtration through a glass filter pad. A little water may be necessary to solubilize crystallized silver methanesulfonate. The collected aqueous silver methanesulfonate solution may be used as is, or the solution may be evaporated to yield solid silver methanesulfonate.

The following table sets forth the practical and preferred parameters for the reactants and conditions of the process of this invention.

| Parameter | Practical Range | Preferred Range |
|---|---|---|
| Temperature | 5° C.–150° C. | 10° C.–80° C. |
| Pressure | 0.1 atm–10 atm | approx. 1 atm |
| Reaction Time | 1 hour–500 hours | 4 hrs–48 hrs |
| Oxidant Addition | controlled so as the reaction temperature does not exceed 20° C. above setpoint (preferred) or 50° C. above setpoint (practical) | |
| Agitation | mild to vigorous | vigorous |
| Reactants, Mole-Ratios | | |
| Oxidizing Agent/Ag | 100/1–1/1 | 6/1–1/1 |
| Sulfonic Acid/Ag Reactants | 100/1–1/1 | 2/1–1/1 |
| Oxiding Agents | $H_2O_2$ $RSO_2OOSO_2R$ $HNO_3$ $Mn(VII)$ $Ce(IV)$ etc. | $H_2O_2$ $RSO_2OOSO_2R$ |
| Sulfonic Acids (aqueous) | Linear $C_1$–$C_{20}$ alkane, branched chain $C_3$–$C_{40}$ alkane (substituted or unsubstituted) 1%–100% (weight) | $C_1$–$C_3$ alkane 50%–90% (weight) |
| Silver (Ag) | metallic silver in various physical forms | metallic silver with specific surface area of 200 cm$^2$ per gram or higher |
| Precious Metals | metallic material in various physical forms | metallic material with specific surface area of 200 cm$^2$/g. or higher |

The following examples are set forth to further demonstrate the process of this invention.

EXAMPLE 1

Comparative Preparation of Silver Methanesulfonate (AgOMs) Crystals via $Ag_2O$

A 1 gallon beaker was charged with 500 grams of 70% aqueous MSA (3.64 moles, 1752 grade Elf Atochem N.A., Inc.). To the MSA was added 402 grams of $Ag_2O$ (Technic, Inc., 3.47 moles of $Ag^+$) over 1 hour. The mixture was stirred by hand with a Teflon® rod, and the temperature was maintained at about 50° C. for most of the addition. Following the addition, the mixture was stirred at room temperature for 1 hour. The reaction solution was filtered twice through 1.5 micron glass fibre filter pads, and the filtrate was evaporated to dryness in vacuo. The isolated solid was washed with 1000 ml of isopropanol (i-PrOH) while being collected by vacuum filtration.

Yield=450 grams AgOMs
Theoretical=704 grams
% Yield=64%
AgOMs recovered from i-PrOH=50 grams
Balance of Ag=residual silver oxide
Analysis:

|  | Theoretical | Actual |
| --- | --- | --- |
| % Ag | 53.15 | 54.80% |
| % S | 15.80% | 16.48% |
| % C | 5.92% | 5.85% |

It should be noted that the AgOMs prepared by this procedure often has a dark caste. The dark caste results from small amounts of unreacted silver oxide passing through the filter membranes which are commonly used to remove residual solid materials from reaction solutions. Furthermore, the reaction only proceeds to about 75% of completion under the conditions described above. On the other hand, the direct peroxidic oxidation of silver metal (see Examples below) produces AgOMs which is pure and completely white in color.

EXAMPLE 2

Direct Preparation of Silver Methanesulfonate Acid AgOMs) from Silver Metal

A beaker was charged with 108 grams of Ag metal (Johnson Matthey Ltd. of Brampton, Ontario, CN, −10/+40 needles, 1 mole) and 200 ml of 70% aqueous MSA (2 moles, 1752 grade). The mixture was vigorously stirred and 171 grams of 30% aqueous $H_2O_2$ (1.5 mole, 3 equivalent) was added at such a rate that the temperature was maintained below 35° C. (ice cooling can be used). Following peroxide addition, the solution was allowed to stir at room temperature until all the oxidant had been consumed. The oxidant content of the solution was monitored with an iodide color test. The inefficiency in oxidant use was mostly due to decomposition of the peroxide to oxygen, and excessive frothing of the solution ($O_2$ evolution) was sometimes observed. Following addition and reaction of the peroxide, the solution was filtered through a 1 micron glass fiber filter element and concentrated to near saturation. The solution was analyzed for silver content using an ICP/emission technique*. Aqueous solutions of silver mesylate (AgOMs) with concentrations in excess of 400 g/l $Ag^+$[as metal] could be obtained with this method. A 400 g/l ($Ag^+$) [as metal] solution would be an ideal commercial silver supply for a methanesulfonic acid (MSA) based silver plating bath.

*-See: A monograph entitled "Inductively Coupled Plasma Emission Spectroscopy" Part 1, pp. 109–111, in Chemical Analysis, Vol. 90, John Wiley & Sons (1987)

The data below is representative of the experimental results obtained for a process similar to the one above carried out with silver metal of different physical forms (types):

| Ag type | Ag Used | [O] equiv. | Time | Ag+ |
| --- | --- | --- | --- | --- |
| 237 Flake | 5.6g | 4 | 30 min. | 5.6g |
| Ag coins | 0.1g | 110 | 10 hr. | 0.1g |
| Needle Ag (−10/+40) | 2.7g | 8 | 48 hr. | 2.7g |
| Needle Ag (−60/+100) | 5.5g | 3 | 24 hr. | 5.5g |

Ag Type=physical form of silver used for the oxidation
Ag Used=weight of silver consumed
[O] equiv]=number of equivalents of peroxide used relative to the amount of Ag consumed.
Time=total time necessary for the oxidation.
Ag+=amount of silver ion in aqueous solution (by ICP-emission). This number was used to insure that the amount of silver consumed was balanced by the amount of argentous ion in solution.
237 Flake=high surface area silver powder obtained from Technic, Inc. of Cranston, R.I.
Ag Coins=Ag pieces formed by cutting and mechanically flattening silver ingots.
Needle Ag=electrocrystallized silver needles obtained from Handy & Harmon of Fairfield, Conn.
Numerical designations refer to mesh sizes (i.e., −60/+100 refers to silver needles which passed through a −60 mesh screen but were retained by a 100 mesh screen).

EXAMPLE 3

Preparation of AgOMs Crystals via Silver Metal

A 1 liter beaker was charged with 120 grams of silver needles (Handy & Harmon, −60/+100 mesh, 1.11 moles) and 105 ml of 1752 grade 70% aqueous MSA (app. 1.00 mole). To this was added 150 grams of 30% aqueous $H_2O_2$ (1.32 moles, 2.64 equiv.) at such a rate that the temperature of the solution was maintained below 40° C. The mixture was stirred at room temperature for 24 hours (foil was wrapped around the beaker to shelter it from light.) Another 100 grams of 30% aqueous $H_2O_2$ (0.88 moles, 1.76 equivalents) was added (temperature maintained below 40° C. as before), and the solution was stirred at room temperature for another 72 hours. The solution was assayed for excess oxidant with an iodide color test, and following a negative test for excess oxidant the solution was filtered through a 1 micron glass fibre pad (10 grams of metallic silver was recovered). The filtered solution was evaporated to dryness in vacuo (note that all excess oxidant must be consumed prior to evaporating the solution to dryness), and the solid product was washed with 200 ml of i-PrOH while being collected by vacuum filtration.

Yield=185 grams AgOMs
Theoretical=203 grams
% Yield=91%
AgOMs recovered from i-PrOH=17 grams
Balance of Ag=mechanical losses
Analysis:

| Analysis: | | |
| --- | --- | --- |
|  | Theoretical | Actual |
| % Ag | 53.15% | 54.80% |
| % S | 15.80% | 16.48% |
| % C | 5.92% | 5.92% |

The purity of the AgOMs produced by the above method was also verified by NMR and IC (ion chromatographic) methods.

The synthetic method described herein allows for a number of precious metal salts, particularly silver alkanesulfonates, to be prepared more economically than was previously possible. The disclosed process will make the silver salts of nonoxidizing acids less expensive to purchase, and the availability of less expensive silver salts should, in turn, encourage the further development of novel applications of such salts. One application of note is the electroplating of silver and silver alloys from noncyanide electrolytes (i.e., aqueous solutions containing no cyanide). The current fabrication cost (i.e., cost in excess of the silver) of silver cyanide is significantly lower than the fabrication cost of alternative noncyanide salts. The present invention describes a method of producing the silver salts of certain nonoxidizing acids, particularly alkanesulfonic acids and preferably methanesulfonic acid, at a fabrication cost which is competitive with the fabrication cost for silver cyanide. Competitive prices for water soluble noncyanide silver salts, such as silver methanesulfonate, will likely encourage the further development of economically competitive and environmentally safe noncyanide silver plating processes.

As previously indicated, this invention relates to a process of synthesizing precious metal salts of nonoxidizing acids. Silver has been used in the examples and the detailed explanation of the invention to represent precious metals generally. Such metals, other than silver, include, for example, platinum, gold, palladium, rhodium, iridium, osmium and ruthenium. It is anticipated that these metals will react in the process of this invention to prepare the corresponding salts.

I claim:

1. A process for the direct synthesis of a precious metal salt of a nonoxidizing acid comprising reacting together a precious metal and an oxidizing agent in the presence of a substituted or unsubstituted $C_1$–$C_{40}$ alkanesulfonic acid.

2. The process of claim 1 wherein the precious metal is silver.

3. The process of claim 1 wherein the precious metal is platinum.

4. The process of claim 1 wherein said nonoxidizing acid is a linear $C_1$–$C_{20}$ alkanesulfonic acid.

5. The process of claim 1 wherein said nonoxidizing acid is a branched chain $C_3$–$C_{40}$ alkanesulfonic acid.

6. The process of claim 1 wherein said nonoxidizing acid is an alkanesulfonic acid wherein said alkane group contains substituent functional radicals.

7. The process of claim 6 wherein said functional radicals are hydroxyl, keto or nitro radicals.

8. The process of claim 1 wherein said oxidizing agent is hydrogen peroxide.

9. The process of claim 1 wherein said oxidizing agent is a peroxidic compound.

10. The process of claim 1 wherein said oxidizing agent is a dialkanesulfonyl peroxide.

11. The process of claim 2 wherein said silver metal is electrocrystallized needles obtained from silver refining.

12. The process of claim 2 wherein said silver metal is obtained by electrodeposition of Ag on a cathode material.

13. The process of claim 2 carried out in conjunction with a silver ore refining operation.

14. The process of claim 2 wherein said silver metal has a specific surface area of at least 100 $cm^2/g$.

15. The process of claim 2 wherein the reaction is carried out at a temperature within the range of from 5° to 150° C.

16. The process of claim 15 wherein the reaction pressure ranges from 0.1 atmosphere to 10 atmospheres and the reaction time ranges from 1 hour to 21 days.

17. A process for the direct synthesis of a silver salt of a linear $C_1$–$C_3$ alkanesulfonic acid comprising reacting together silver metal needles having a mesh size ranging from 8 to 100 with a linear $C_1$–$C_3$ alkanesulfonic acid at an acid to silver weight ratio ranging from about 2:1 to about 1:1, a temperature ranging from about 10° C. to about 80° C., a pressure ranging from about 0.1 to about 10 atmospheres, and for a time ranging from about 4 hours to about 48 hours, in the presence of hydrogen peroxide at a total peroxide to silver mole ratio ranging from about 6:1 to about 1/2:1.

18. The process of claim 17 wherein said hydrogen peroxide is contained in an aqueous solution.

19. The process of claim 18 wherein said alkanesulfonic acid is contained in an aqueous solution.

20. The process of claim 19 wherein said alkanesulfonic acid is methanesulfonic acid.

21. The process of claim 1 wherein the source of said precious metal includes a mixture of at least one precious metal or its salt and at least one other metal or its salt.

22. The process of claim 2 wherein the source of said silver includes a mixture of silver metal or its salt and at least one other metal or its salt.

23. The process of claim 22 wherein the other metal is a precious metal.

* * * * *